(12) United States Patent
Schleich et al.

(10) Patent No.: US 8,577,473 B2
(45) Date of Patent: Nov. 5, 2013

(54) COCHLEAR IMPLANT STIMULATION WITH LOW FREQUENCY CHANNEL PRIVILEGE

(75) Inventors: Peter Schleich, Telfs (AT); Dirk Meister, Axams (AT); Peter Nopp, Birgitz (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 437 days.

(21) Appl. No.: 12/873,438

(22) Filed: Sep. 1, 2010

(65) Prior Publication Data

US 2011/0004274 A1 Jan. 6, 2011

Related U.S. Application Data

(63) Continuation-in-part of application No. 11/872,983, filed on Oct. 16, 2007, now Pat. No. 7,941,223, which is a continuation-in-part of application No. 11/076,446, filed on Mar. 8, 2005, now Pat. No. 7,283,876, application No. 12/873,438, which is a continuation-in-part of application No. 12/267,858, filed on Nov. 10, 2008.

(60) Provisional application No. 60/551,318, filed on Mar. 8, 2004, provisional application No. 60/986,690, filed on Nov. 9, 2007.

(51) Int. Cl.
*A61N 1/08* (2006.01)

(52) U.S. Cl.
USPC ............... 607/55; 607/56; 607/57; 607/136; 607/137; 600/379; 600/559

(58) Field of Classification Search
USPC ......... 607/55, 56, 57, 136, 137; 600/379, 559
See application file for complete search history.

(56) References Cited

U.S. PATENT DOCUMENTS

| 4,284,856 A | 8/1981 | Hochmair et al. ......... 179/107 E |
| 4,428,377 A | 1/1984 | Zollner et al. ................. 128/419 |

(Continued)

FOREIGN PATENT DOCUMENTS

| WO | WO 99/35882 | 7/1999 | ............. H04R 25/00 |
| WO | WO 99/49815 | 10/1999 | ................. A61F 2/18 |

(Continued)

OTHER PUBLICATIONS

Grayden, et al, "A Cochlear Implant Speech Processing Strategy Based on an Auditory Model", *Proceedings of the 2004 Intelligent Sensors Sensors Networks and Information Processing Conference*, Dec. 14-17, 2004; pp. 491-496.

(Continued)

*Primary Examiner* — Christopher D Koharski
*Assistant Examiner* — Natasha Patel
(74) *Attorney, Agent, or Firm* — Sunstein Kann Murphy & Timbers LLP

(57) ABSTRACT

A system and method for activating stimulation electrodes in cochlear implant electrode is described. A preprocessor filter bank processes an input acoustic audio signal to generate band pass signals that each represent an associated band of audio frequencies. An information extractor extracts stimulation signal information from the band pass signals based on assigning the band pass signals to corresponding electrode stimulation groups that each contain one or more stimulation electrodes, and generates a set of stimulation event signals for each electrode stimulation group that define electrode stimulation timings and amplitudes. A pulse selector selects a set of electrode stimulation signals from the stimulation event signals based on a pulse weighting function that uses channel-specific weighting factors favoring lower frequencies for activating the stimulation electrodes to stimulate neighboring audio nerve tissue.

69 Claims, 5 Drawing Sheets

(56) References Cited

U.S. PATENT DOCUMENTS

| | | | |
|---|---|---|---|
| 4,515,158 A | 5/1985 | Patrick et al. | 128/419 R |
| 4,532,930 A * | 8/1985 | Crosby et al. | 607/57 |
| 5,215,085 A | 6/1993 | Von Wallenberg-Pachaly | 128/420.6 |
| 5,601,617 A | 2/1997 | Loeb et al. | 607/56 |
| 5,938,691 A | 8/1999 | Schulman et al. | 607/57 |
| 6,175,767 B1 | 1/2001 | Doyle, Sr. | 607/57 |
| 6,219,580 B1 | 4/2001 | Faltys et al. | 607/57 |
| 6,289,247 B1 | 9/2001 | Faltys et al. | 607/57 |
| 6,295,472 B1 | 9/2001 | Rubinstein et al. | 607/55 |
| 6,594,525 B1 | 7/2003 | Zierhofer | 607/57 |
| 6,600,955 B1 | 7/2003 | Zierhofer | 607/57 |
| 7,039,466 B1 * | 5/2006 | Harrison et al. | 607/56 |
| 7,209,789 B2 | 4/2007 | Zierhofer | 607/57 |
| 2005/0107843 A1 | 5/2005 | McDermott et al. | 607/57 |
| 2005/0203589 A1 | 9/2005 | Zierhofer | 607/57 |
| 2006/0052841 A1 | 3/2006 | Daly et al. | 607/57 |
| 2006/0080087 A1 | 4/2006 | Vandali et al. | 704/207 |
| 2006/0227986 A1 * | 10/2006 | Swanson et al. | 381/312 |
| 2006/0265061 A1 | 11/2006 | Kwon et al. | 623/10 |
| 2007/0156202 A1 | 7/2007 | Zierhofer | 607/57 |
| 2009/0018614 A1 * | 1/2009 | Zierhofer | 607/56 |

FOREIGN PATENT DOCUMENTS

| | | | |
|---|---|---|---|
| WO | WO 01/19135 | 3/2001 | H04R 25/00 |
| WO | WO 01/19304 | 3/2001 | A61F 11/04 |
| WO | WO 2006/119069 | 11/2006 | |

OTHER PUBLICATIONS

Kral, A., et al, "Spatial resolution of cochlear implants: The electrical field and excitation of auditory afferents", *Hearing Research*, vol. 121 (1998, pp. 11-28.

Loizou, P.C. "Signal Processing for Cochlear Prosthesis: A Tutorial Review", *IEEE*, Jan. 1997, pp. 881-885; 0-7803-3694-1/97.

Loizou, P.C., "Signal-Processing Techniques for Cochlear Implants", *IEEE Engineering in Medicine and Biology*, May/Jun. 1999, pp. 34-46.

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

Secker-Walker, H., et al, "Time-domain analysis of auditory-nerve-fiber firing rates", *J. Acoust. Soc. Am.* 88(3), pp. 1427-1436 (1990).

Sit., J., et al "A Low-Power Asynchronous Interleaved Sampling Algorithm for Cochlear Implants that Endoes Enelope and Phase Information", *IEEE Trans Biomed Eng.*, Jan. 2007; 54(1), pp. 138-149.

Vandali, A., et al, "Pitch ranking ability of cochlear implant recipients: A comparison of sound-processing strategies", *Accoust Soc. Am.*, May 2005; 117(5); pp. 3126-3138.

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Wilson, B. S., et al "Temporal Representations With Cochlear Implants", *The American Journal of Otology*, 18:530-534, 1997.

Ziese, M., et al, "Speech Understanding with the CIS and the n-of-m Strategy in the MED-EL COMBI 40+ System", *ORL*, 2000;62:321-329.

\* cited by examiner $$30\begin{cases} \text{i.} [\ 1]_{1S} \\ \text{ii.} [\ 2]_{1S} \\ \text{iii.} [\ 3]_{1S} \\ \text{iv.} [\ 4]_{1S} \\ \text{v.} [\ 5]_{1S} \\ \text{vi.} [\ 6]_{1S} \\ \text{vii.} [\ 7]_{1S} \\ \text{viii.} [\ 8]_{1S} \\ \text{ix.} [\ 9]_{1S} \\ \text{x.} [10]_{1S} \\ \text{xi.} [11]_{1S} \\ \text{xii.} [12]_{1S} \end{cases}$$

FIG. 3

$$40\ \text{i.} [1\ 2\ 3\ 4\ 5\ 6\ 7\ 8\ 9\ 10\ 11\ 12]_{6S}$$

FIG. 4

$$50\begin{cases} \text{i.} [\ 1\ 2]_{1S} \\ \text{ii.} [\ 3\ 4]_{1S} \\ \text{iii.} [\ 5\ 6]_{1S} \\ \text{iv.} [\ 7\ 8]_{1S} \\ \text{v.} [\ 9\ 10]_{1S} \\ \text{vi.} [11\ 12]_{1S} \end{cases}$$

FIG. 5

$$60\begin{cases} \text{i.} [\ 1\ 2]_{2S} \\ \text{ii.} [\ 3\ 4]_{1S} \\ \text{iii.} [\ 1\ 2]_{2S} \\ \text{iv.} [\ 5\ 6]_{1S} \\ \text{v.} [\ 1\ 2]_{2S} \\ \text{vi.} [\ 7\ 8]_{1S} \\ \text{vii.} [\ 1\ 2]_{2S} \\ \text{viii.} [\ 9\ 10]_{1S} \\ \text{ix.} [\ 1\ 2]_{2S} \\ \text{x.} [11\ 12]_{1S} \end{cases}$$

FIG. 6

$$70\begin{cases} \text{i.} [1\ 2\ 4\ 6]_{2S} \\ \text{ii.} [2\ 9\ 12]_{1S} \\ \text{iii.} [1\ 5\ 10\ 11\ 12]_{2P} \end{cases}$$

FIG. 7

1000
i. [CH(1)*w(1)  CH(2)*w(2)]  1S
ii. [CH(3)*w(3)  CH(4)*w(4)]  1S
iii. [CH(5)*w(5)  CH(6)*w(6)]  1S
iv. [CH(7)*w(7)  CH(8)*w(8)]  1S
v. [CH(9)*w(9)  CH(10)*w(10)]  1S
vi. [CH(11)*w(11)  CH(12)*w(12)]  1S

FIG. 10

1100
i. [CH(1)*w(1)  CH(2)*w(2)  CH(3)*w(3)
   CH(4)*w(4)  CH(5)*w(5)  CH(6)*w(6)]  2P
ii. [CH(7)*w(7)  CH(8)*w(8)]  1S
iii. [CH(9)*w(9)  CH(10)*w(10)]  1S
iv. [CH(11)*w(11)  CH(12)*w(12)]  1S

COCHLEAR IMPLANT STIMULATION WITH LOW FREQUENCY CHANNEL PRIVILEGE

This application a continuation-in-part of co-pending U.S. application Ser. No. 11/872,983, filed Oct. 16, 2007, which in turn is a continuation-in-part of U.S. application Ser. No. 11/076,446, filed Mar. 8, 2005, now issued as U.S. Pat. No. 7,283,876, which in turn claimed priority from U.S. Provisional Patent Application 60/551,318, filed Mar. 8, 2004; and this application also is a continuation-in-part of co-pending U.S. application Ser. No. 12/267,858, filed Nov. 10, 2008, which in turn claimed priority from U.S. Provisional Patent Application 60/986,690, filed Nov. 9, 2007; the contents of all of which are hereby incorporated by reference.

FIELD OF THE INVENTION

The present invention relates to signal processing for stimulation of cochlear implant electrodes.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window membrane openings of the cochlea 104. The cochlea 104 is a narrow fluid-filled duct that is wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that electrically stimulates auditory nerve tissue with small currents delivered by multiple electrode contacts distributed along an implant electrode. FIG. 1 also shows some components of a typical cochlear implant system where an external microphone provides an audio signal input to an external signal processing stage 111 which implements one of various known signal processing schemes. The processed audio signal is converted by the external signal processing stage 111 into a digital data format for transmission into an implant stimulator 108. Besides extracting the audio information, the implant stimulator 108 may perform additional signal processing such as error correction, pulse formation, etc., and produces a stimulation pattern (based on the extracted audio information) that is sent through connected wires 109 to an implant electrode 110. Typically, the implant electrode 110 includes multiple stimulation electrodes on its surface that provide selective stimulation of the cochlea 104.

In cochlear implants, a relatively small number of stimulation electrodes are each associated with relatively broad frequency bands, with each stimulation electrode addressing a group of neurons with a stimulation pulse the charge of which is derived from the instantaneous amplitude of the signal envelope within the associated frequency band. In some coding strategies, stimulation pulses are applied at a constant rate across all stimulation electrodes, whereas in other coding strategies, stimulation pulses are applied at an electrode-specific rate.

One problem in cochlear implants is that of spatial channel interaction. Spatial channel interaction means that there is significant geometric overlapping of electrical fields at the location of the excited nervous tissue, if multiple different stimulation electrodes are activated at around the same time. Spatial channel interaction is primarily due to the conductive fluids and tissues surrounding the implant electrode 110.

One successful stimulation strategy is "Continuous-Interleaved-Sampling" (CIS) as introduced by Wilson at al., Better Speech Recognition with Cochlear Implants, Nature, vol. 352, 236-238, July 1991; incorporated herein by reference. CIS signal processing typically involves:

(1) splitting up of the audio frequency range into spectral bands by means of a filter bank;
(2) envelope detection of each filter output signal; and
(3) instantaneous nonlinear compression of the envelope signal (map law).

Based on the tonotopic organization of the cochlea, each stimulation electrode in the scala tympani is associated with a band pass filter of the external filter bank and symmetrical biphasic current pulses are applied as stimulation. The amplitudes of the stimulation pulses are directly obtained from the compressed envelope signals (step (3) above). These signals are sequentially sampled and the stimulation pulses are applied in a strictly non-overlapping sequence. Thus, spatial channel interaction is minimized and a comparatively precise definition of electrical fields in the cochlea is achieved. For example, consider a 12-channel CIS-system with a maximum overall stimulation rate of 18 kpps; assuming that each channel is addressed once in a cycle, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which approaches the lower limit.

A stimulation strategy related to CIS is the "N-of-M" strategy, wherein only the N electrode channels with maximum energy are selected out of the total number of M band pass signal channels during each stimulation cycle, as described by Wilson et al., *Comparative Studies Of Speech Processing Strategies For Cochlear Implants*, Laryngoscope 1998; 98:1069-1077; incorporated herein by reference. Typically, the number of band pass signal channels M is constant and equal to the overall number of usable channels. Thereby the instantaneous stimulation rate of a selected channel is increased by a factor of M/N. Interestingly, N of M strategies do not seem not to improve speech perception as compared to standard CIS, as described in Ziese et al., *Speech Understanding With CIS And N-Of-M Strategy In The MED-EL COMBI 40+ System*, ORL 2000; 62:321-329; incorporated herein by reference.

One disadvantage of N-of-M strategies (with constant M) is that neurons or groups of neurons may suffer "microshocks" if electrode channels are switched from "inactive" to "active". For example, consider a situation where a train of supra-threshold stimulation pulses is applied at a particular stimulation electrode. The initial pulse will cause action potentials in most of the neighboring neurons, followed by a refractory period during which a more limited neural response can be elicited. Most of the neurons will continue to be in similar refractory states until enough time has passed to cause a sufficient distribution of refractory states. Thus, for at least an initial period of time, most of the neurons will respond in the same manner to each pulse due to their similar refractory state, as described by Wilson et al., *Temporal Representation With Cochlear Implants*, Am. J. Otology, Vol. 18, No. 6 (Suppl), S30-S34, 1997; incorporated herein by reference.

In conventional CIS, periods with no activity at particular stimulation electrodes do not occur since each electrode is stimulated in each cycle and minimum pulse amplitudes are usually close to or slightly above thresholds. So even when there is no spectral energy present in a particular frequency band, the associated electrode will be active keeping neurons in different refractory states. In addition, a number of neurons may be kept busy because of activity in neighboring channels. In this respect, spatial channel interaction can have an (unintentional) advantageous effect.

Another issue with N-of-M stimulation is the tendency for higher frequency signal channels to dominate over low frequency stimulation channels. This effect is especially unfortunate because of the fact that the lower frequency signal channels contain the fundamental frequency of the overall audio signal, which is the most dominant cue for speech understanding.

SUMMARY OF THE INVENTION

Embodiments of the present invention are directed to systems, methods and computer program products for activating stimulation electrodes in cochlear implant electrode. A preprocessor filter bank processes an input acoustic audio signal to generate band pass signals that each represent an associated band of audio frequencies. An information extractor extracts stimulation signal information from the band pass signals based on assigning the band pass signals to corresponding electrode stimulation groups that each contain one or more stimulation electrodes, and generates a set of stimulation event signals for each electrode stimulation group that define electrode stimulation timings and amplitudes. A pulse selector selects a set of electrode stimulation signals from the stimulation event signals based on a pulse weighting function that uses channel-specific weighting factors favoring lower frequencies for activating the stimulation electrodes to stimulate neighboring audio nerve tissue. In further specific embodiments, there may also be a pulse shaper for developing the electrode stimulation signals into a set of output electrode pulses to the stimulation electrodes based on patient specific factors.

The pulse selector may select the set of electrode stimulation signals in a recurring stimulation cycle based on the electrode stimulation groups. For example, so as to sequentially activate a single stimulation electrode in each electrode stimulation group in each stimulation cycle, or to simultaneously activate at least two stimulation electrodes in at least one of the electrode stimulation groups in each stimulation cycle. Or, for at least one stimulation group the pulse selector may vary over time which specific stimulation electrodes are activated in each stimulation cycle.

The information extractor may generate the stimulation event signals based on a group pulse rate defined for each electrode stimulation group. The pulse selector may generate the electrode stimulation signals for each electrode stimulation group based on one or more non-linear response characteristics of the stimulated nerve tissue. For example, the one or more non-linear response characteristics may reflect spatial interaction between the stimulation electrodes.

The pulse selector may select the electrode stimulation signals so as to sequentially activate the stimulation electrodes within each electrode stimulation group. Or the pulse selector may select the electrode stimulation signals so as to simultaneously activate the stimulation electrodes within at least one electrode stimulation group. 12. The pulse weighting function may use channel specific weighting factors that are constant over time or that vary over time.

BRIEF DESCRIPTION OF THE DRAWINGS

FIG. 3 shows an example of selected groups in a conventional CIS system (Prior Art).

FIG. 4 shows an example of selected groups based on an N-of-M strategy (Prior Art).

FIG. 5 shows an example of selected groups providing constant activity in all cochlear regions.

FIG. 6 shows an example of selected groups that provides good temporal representation.

FIG. 7 shows an example of selected groups that include simultaneous stimulation.

FIG. 10 shows an example of selected stimulation groups extended with weighting factors to emphasize lower frequency channels.

FIG. 11 shows an example of selected stimulation groups extended with a different scheme of weighting factors to emphasize lower frequency channels.

DETAILED DESCRIPTION OF SPECIFIC EMBODIMENTS

Embodiments of the present invention are direct to techniques for activating electrodes in an implanted electrode array. As compared to Continuous-Interleaved-Sampling (CIS) approaches, higher stimulation rates can be used while avoiding, for example, "micro-shocks" encountered in an N-of-M strategy. Signals in higher frequency FSP channels deliver more zero-crossings and therefore more pulses than lower frequency channels. Without a privilege for low frequency channels, the proportional loss of pulses due to the N-of-M selection is higher for low frequency channels then for the higher channels. Low frequency channels are therefore more affected by signal distortion due to an N-of-M selection (assuming equal amplitudes in the channels).

Figure 9:
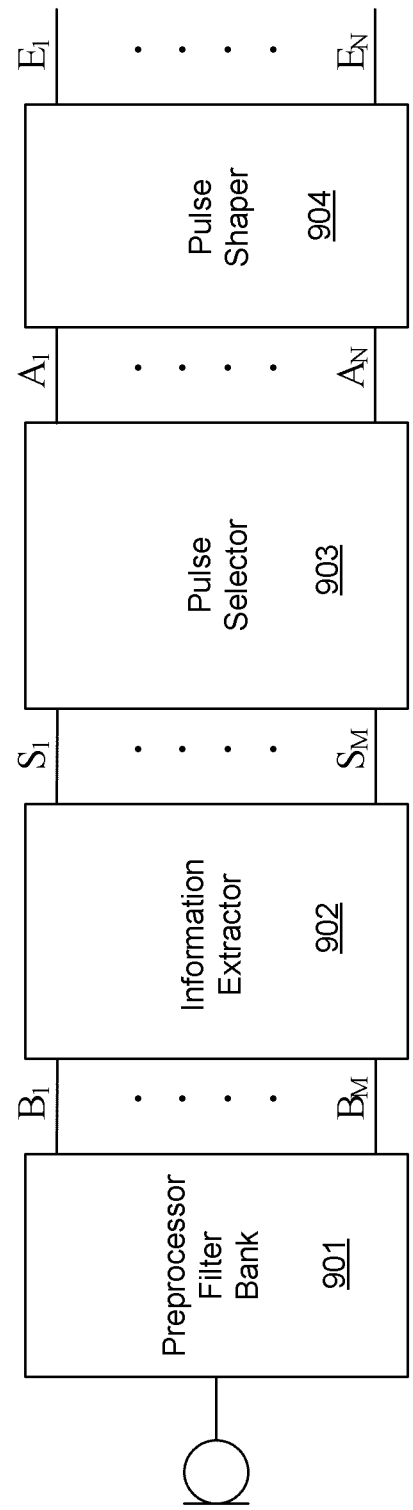
FIG. 9 shows functional signal processing blocks in a typical N of M cochlear implant system.

FIG. 9 shows the major functional signal processing blocks in a typical embodiment where Preprocessor Filter Bank 901 is a bank of parallel frequency-specific signal filters with each filter being associated with a specific band of audio frequencies. Thus, an input acoustic audio signal is filtered into some M band pass signals, $B_1$ to $B_M$ where each signal corresponds to the band of frequencies for one of the band pass filters. Typically, the Preprocessor Filter Bank 901 has a high number of narrow frequency band filters for differentiating and mapping the analyzed frequency range. Preprocessor Filter Bank 901 also is designed to apply some initial pre-processing to the input acoustic audio signal, e.g., automatic gain control, noise reduction, etc.

The band pass signals $B_1$ to $B_M$ are then input to an Information Extractor 902 which extracts signal specific stimulation information—e.g., envelope information, phase information, timing of requested stimulation events, etc.—into a set of M stimulation event signals $S_1$ to $S_M$, which represent requested stimulation events. For example, channel specific sampling sequences (CSSS) may be used as described in U.S. Pat. No. 6,594,525, which is incorporated herein by reference. The band pass signals $B_1$ to $B_M$ may be pooled into a smaller number of overlapping macro bands, and within each macro band, the channel with the highest envelope is selected for a given sampling interval. The stimulation event signals $S_1$ to $S_M$ may also be decimated based on channel interaction and inhibition functions to extract the temporal fine structure of the band pass signals.

Pulse Selector 903 weights each requested stimulation event signal $S_1$ to $S_M$ with a weighted matrix of stimulation amplitudes that reflect patient-specific perceptual characteristics to produce a set of N electrode stimulation signals $A_1$ to $A_N$ that provide an optimal electric tonotopic representation of the acoustic signal. Matrix weighting of the stimulation pulses is described further in U.S. Patent Application 61/046,832, filed Apr. 22, 2008, which is incorporated herein by reference. Equation 1 shows a typical weighting matrix of size M×N:

$$W = \begin{pmatrix} 1 & 0.923 & 0.846 & \ldots & \ldots & 0 & 0 & 0 \\ 0 & 0.077 & 0.154 & \ldots & \ldots & 0 & 0 & 0 \\ 0 & 0 & 0 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.154 & 0.077 & 0 \\ 0 & 0 & 0 & \ldots & \ldots & 0.846 & 0.923 & 1 \end{pmatrix} \quad \text{Equation 1}$$

where N is the number of independently addressable stimulation electrodes, and M is the number of analysis filter bands. A negative weighting factor $W_{ij}$ indicates an inverted electrical pulse.

Finally, patient-specific stimulation is achieved by individual amplitude mapping and pulse shape definition in Pulse Shaper 904 which develops the set of electrode stimulation signals $A_1$ to $A_N$ into a set of output electrode pulses $E_1$ to $E_N$ to the electrodes in the implanted electrode array which stimulate the adjacent nerve tissue. Whenever one of the requested stimulation event signals $S_1$ to $S_M$ requests a stimulation event, the respective number of electrodes is activated with a set of output electrode pulses $E_1$ to $E_N$. This arrangement can be used to individually adjust the mapping of analysis bands to stimulation sites along the cochlea.

Referring to the typical N of M system depicted in FIG. 9, in illustrative embodiments of the present invention, the band pass signals are assigned to electrode stimulation groups that contain one or more corresponding stimulation electrodes, wherein at least one of the electrode stimulation groups has multiple electrodes, step 201. The selected electrode stimulation groups may be predefined, and stored for example, in a memory device such as a diskette, a fixed disk, a Compact Disk (CD), Read Only Memory (ROM), Erasable Programmable Read-Only Memory (EPROM), and/or Random Access Memory (RAM). As described in more detail in Example 3 below, the electrode stimulation groups may be selected such that the spatial channel interaction between the channels in a given group ensures constant activity in all cochlear areas.

Figure 1:
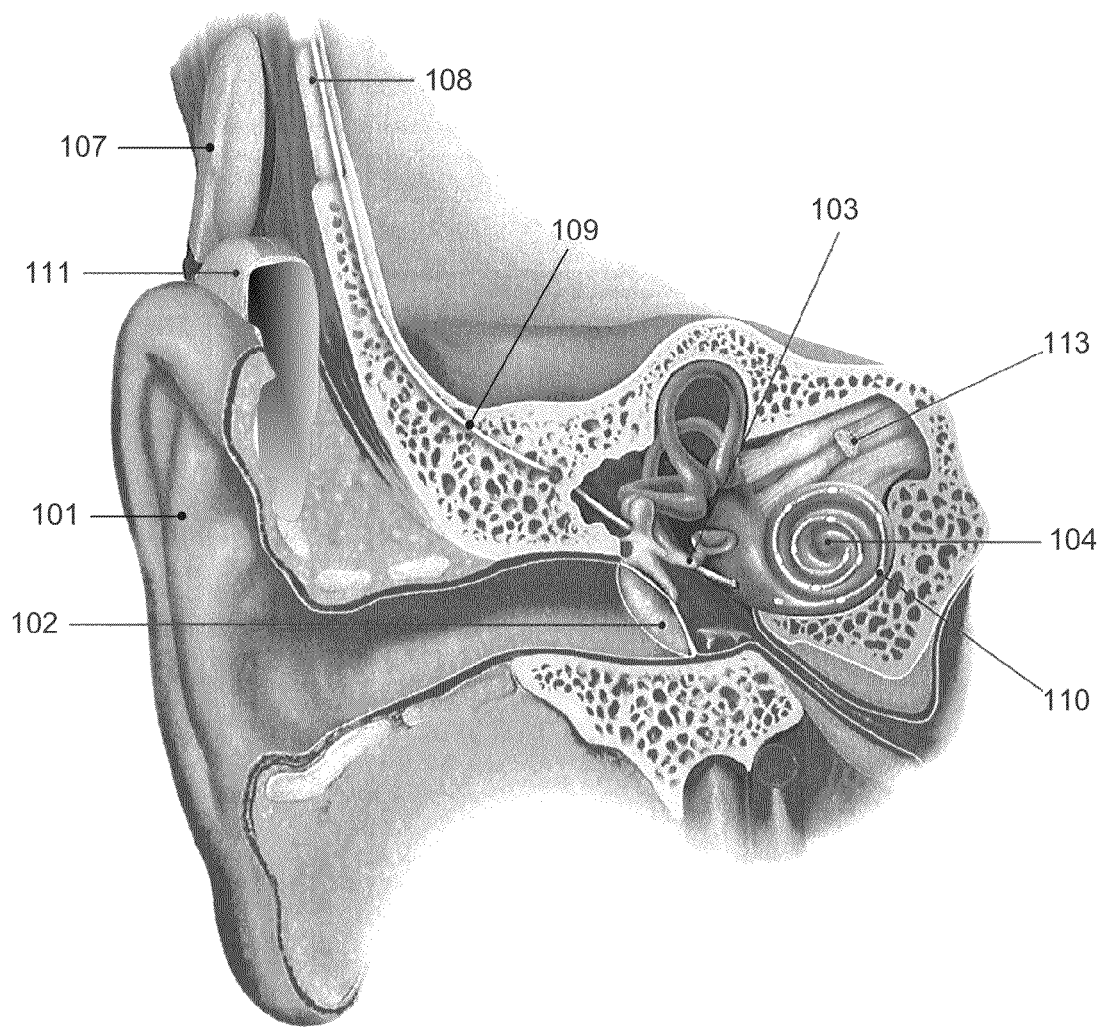
FIG. 1 shows anatomical structures in a human ear and elements of a typical cochlear implant system.
Figure 2:
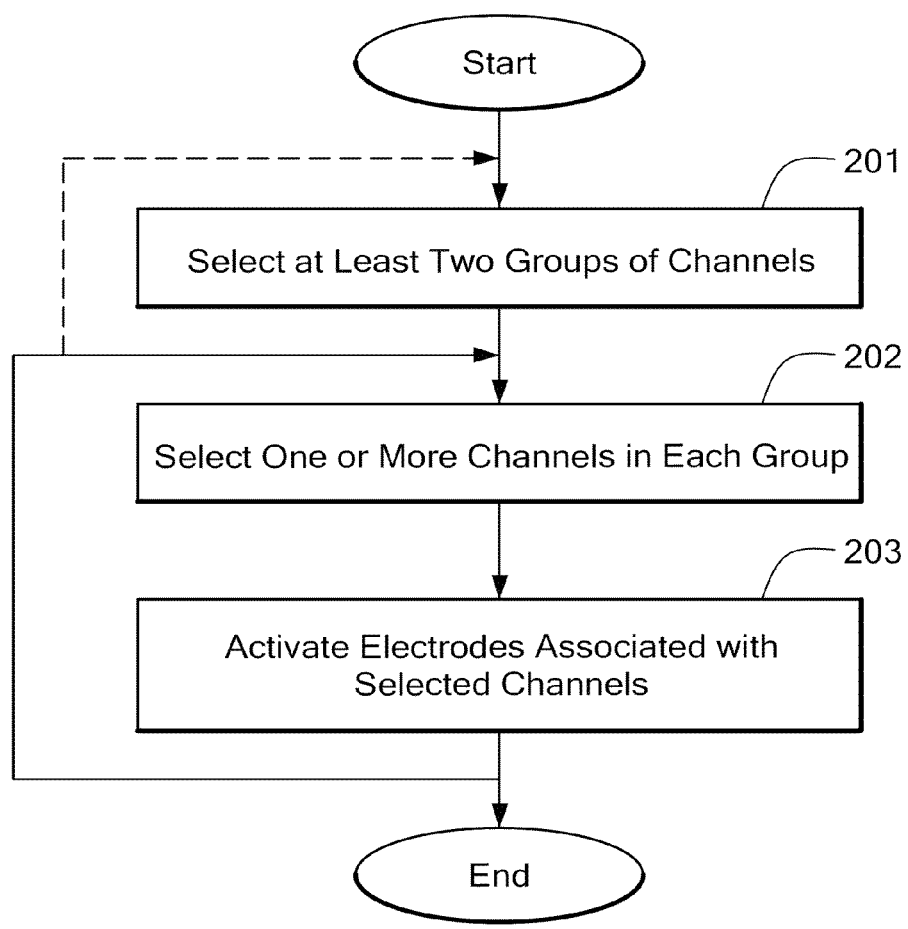
FIG. 2 is a flow chart illustrating a method for activating electrodes in a multi-channel electrode array, in accordance with an embodiment of the invention.

In step 202, at least one band pass signal within each electrode stimulation group is selected as a function of some suitable criteria. For example, the selection may be based on the filter output amplitudes associated with the given band pass signal channels in the group. In various embodiments, the band pass signal channels in the stimulation groups that have the maximum amplitude may be selected. The stimulation electrodes of the selected band pass signal channels are then activated in step 203. The stimulation electrodes of the selected band pass signal channels may be activated sequentially or simultaneously. In the latter case, numerical methods of "channel interaction compensation," may be used, as known in the art and described in U.S. Pat. No. 6,594,525, which is hereby incorporated by reference. The steps of selecting at least one band pass signal channel in each selected stimulation group and activating the stimulation electrodes associated with each selected band pass signal channel are repeated such that that the selected band pass signal channels in at least one selected stimulation group varies. In various embodiments, the selected stimulation groups may also vary over time between stimulation cycles based on any suitable criteria (as illustrated by the dotted line in FIG. 2), while in other embodiments, the selected stimulation groups may remain constant over time.

The following examples describe a 12-channel cochlear implant electrode system with sequential and/or parallel stimulation, where the electrode addresses are within the range [1-12]. Pulses with equal phase durations and a maximum pulse repetition rate R is assumed. Selected stimulation groups are represented within brackets, and the index after the closing bracket represents the number of selected maximum band pass signal channels a within the stimulation group, and whether the selected band pass signal channels are activated sequentially "s" or in parallel "p" (i.e., simultaneously).

Example 1 (Prior Art—"Conventional CIS")

For Example 1, selected stimulation groups in a conventional CIS system are shown in FIG. 3 (Prior Art). One CIS-stimulation cycle includes 12 selected stimulation groups 30. Each selected stimulation group 30 is composed of one band pass channel. Since only one band pass signal channel is present, it is itself the maximum (trivial case). Thus, this setting represents standard 12-channel CIS. The cycle repetition rate is R/12.

Example 2 (Prior Art—"N-of-M")

For Example 2, one stimulation cycle using an N-of-M strategy contains only one selected stimulation group 40, which is composed of all 12 band pass signal channels, as shown in FIG. 4 (Prior Art). The six band pass signal channels with maximum energy are selected. Thus, this setting represents a conventional 6-of-12 setting. The cycle repetition rate is R/6, which is an enhancement by a factor of 2 as compared to Example 1.

Example 3

For Example 3, one stimulation cycle contains six selected stimulation groups 50, as shown in FIG. 5 in accordance with an embodiment of the invention. Each selected stimulation group includes two associated band pass signal channels, and the channel with the greatest amplitude is selected. "CH(i)"

represents the signals feature that is chosen as a selection criteria of the band pass signal channel numbered "i". Traditionally, though not necessarily, this is the signal amplitude. A more advanced processing approach could use a linear combination of multiple signals features, e.g. amplitude and SNR:

$$a(i)*\text{amp}(i)+b(i)*\text{SNR}(i),$$

where amp(i) is the signal amplitude in channel "i", SNR(i) is the signal-to-noise ratio in that channel, and a(i) and b(i) are channel specific constants, derived, for example, during fitting of the implant user. "1S" denotes that 1 channel out of the stimulation group is selected, and the selected channel is stimulated in sequential stimulation mode. If more than one channel is selected, then parallel stimulation mode is also possible, e.g., "2P".

The cycle repetition rate in Example 3 is R/6 which is equal to Example 2. However, an advantage over the conventional N-of-M approach (Example 2) is that permanent activity in all cochlear regions may be realized, comparable to that achieved in standard CIS (Example 1). For example, in standard CIS, channels 1 and 2 are updated with a rate R/12, respectively. Assuming considerable spatial channel interaction between neighboring channels, the "cochlear region" associated to Channels 1 and 2 is thus updated on average by a rate of R/6. In Example 3, one of the two Channels 1 or 2 is selected, and thus the associated cochlear region is also updated with R/6.

Example 4

For Example 4, one stimulation cycle contains ten selected stimulation groups 60, as shown in FIG. 6 in accordance with an embodiment of the invention. Group [1 2] 2S appears 5 times in one stimulation cycle, and both amplitudes are selected. The remaining stimulation groups contain different band pass signal channels, and one maximum channel is selected. This might reflect a situation, where a good temporal representation is especially important for channels 1 and 2 (e.g., apical channels for representation of temporal fine structure), whereas the remaining channels need less temporal resolution. In this setting, channels 1 and 2 are updated with R/3, respectively, whereas the remaining "cochlear regions" are updated with R/15, respectively.

Example 5

For Example 5, a stimulation cycle includes three selected stimulation groups 70, with the two selected band pass signal channels in the third stimulation group activated simultaneously (i.e., in parallel using simultaneous pulses), as shown in FIG. 7 in accordance with an embodiment of the invention. Applying simultaneous pulses advantageously maximizes data transfer time, saving time compared to a sequential pulse sequence. The amplitudes of the simultaneously activated channels in the third group may take into account parameters of spatial channel interaction, and are not limited to channels that have no or minimal spatial channel interaction. Note that a stimulation cycle may include any combination of simultaneous pulses and/or sequential pulses. In Example 5, the selected band pass signal channels in the first two stimulation groups are activated sequentially, with the third stimulation group being activated simultaneously.

As described in U.S. Pat. No. 6,594,525, the simultaneous pulses described in Example 5 may be, without limitation, sign-correlated. As described above, spatial channel interaction means that there is considerable geometric overlapping of electrical fields at the location of the excitable nervous tissue, if different stimulation electrodes (positioned in the scala tympani) are activated. Due to conductivity in the scala tympani, simultaneous stimulation of two or more stimulation electrodes against a remote ground electrode generally results in a temporal mixture of constructive and destructive superposition of electrical fields at the position of the neurons. For example, if two simultaneous stimulation electrodes are activated to produce currents with equal amplitudes, but different signs, most of the current will flow through the shunt conductance between the two stimulation electrodes and will not reach the intended neurons. This additional effect can be removed, if "sign-correlated" pulses are employed. Sign correlated here means that if two or more stimulation pulses occur simultaneously at different stimulation electrodes, positive and negative phases are absolutely synchronous in time. This ensures that the sum of the magnitudes of the single stimulation currents is forced to flow into the reference electrode. Thus, at the site of the excitable neurons, only constructive superposition of currents is possible. The stimulation currents in the sign-correlated pulses may be determined, without limitation, such that at least the potentials at the position of the stimulation electrodes are equal as in the case of single channel stimulation. In various embodiments, it may be assumed that a single electrode causes exponential decays of the potentials at both sides of the stimulation electrode, allowing for a computationally efficient calculation of the pulse amplitudes since a tri-diagonal matrix is involved.

Further specific embodiments of the invention take into account fundamental principles of auditory system response in normal hearing, where the frequency of a given tone affects both the cochlear location where neural response occurs and the temporal characteristics of that neural response. For complex sounds, spectral content is represented in the distribution of cochlear locations where neural responses occur, with the temporal structure of each response being associated with certain spectral components of the sound.

At low intensity levels (low volume), the basilar membrane is relatively sharply tuned so that each nerve fiber ideally picks up the sound component at the characteristic frequency (CF) of the nerve fiber and the temporal response pattern of the nerve fiber also reflects CF. At higher intensity levels (higher volume), however, the basilar membrane exhibits non-linear response with grouping of nerve fibers according to a dominant spectral component in the sound stimulus that is independent of the individual nerve fiber CFs within a group. For example, in response to a speech stimulus, responses of groups of fibers are dominated by a single formant as described in H. E. Secker-Walker and C. L. Searle, *Time-Domain Analysis Of Auditory-Nerve-Fiber Firing Rates*, J. Acoust. Soc. Am. 88:1427-1436, (1990), hereby incorporated by reference. Within each group, all fibers respond to a certain formant ($F_0$ (pitch frequency), $F_1, F_2, F_3$) of the sound stimulus with maximum responses occurring at $F_0$ across all groups. The process can also be explained in reverse—for high stimulus levels, nerve fibers are organized in groups with each group being dominated by a certain feature in the sound stimulus. As stimulus intensity decreases, group size also decreases so that more groups are formed. At low levels, each group ideally consists of nerve fibers which respond to the CF component of the stimulus. Thus nerve fibers respond in groups, with the group size being a function of stimulus intensity as determined by the nonlinear properties of the basilar membrane. Within each group, responses follow a certain dominant feature of the stimulus with the response pattern being amplitude modulated with $F_0$.

Figure 8:
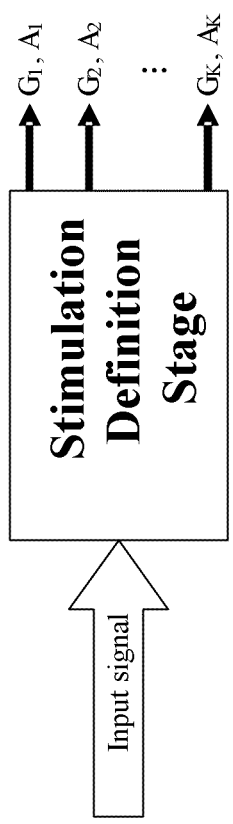
FIG. 8 shows inputs and outputs of a stimulation definition stage according to an embodiment of the present invention.

Accordingly, some specific embodiments of the present invention reflect the physiological processes discussed above and the grouping of nerve fibers according to sound stimulus intensity. Varying the number of stimulated electrodes with stimulation level can better model normal hearing. Without restricting generality, the physiological processes in normal hearing can be modeled by a stimulation definition stage (SDS) based on the non-linear properties of the basilar membrane and the adaptive function of the inner hair cells. For example, as illustrated by the example shown in FIG. 8, based on the input sound signal characteristics (C), the SDS would define G stimulation groups (with G≤M) and assign the M electrode channels to the G groups, and also would define a stimulation amplitude A for each of the G stimulation groups. As an example, for a given input signal at small levels, G=M. For the same signal at higher levels, however, G<M, for example. Other algorithms are also possible, for example, deriving the number of groups and the size of each group as a function of input sound signal characteristics (C) according to a pre-determined relation between the quantities. The SDS would work continuously so that the output of the SDS—e.g., G and A—at each point in time reflects the input sound signal characteristics (C).

In each stimulation group, stimulation pulses can be either applied at a constant rate or at a group-specific rate. The group-specific rate could be derived from an appropriate combination of stimulus features. For example, all stimulation electrodes within a stimulation group could be stimulated at the formant frequency $F_x$ (x=0, 1, 2, . . . ) that the group is associated with. However, for high formant frequencies this could result in stimulation rates which might be greater than a pitch saturation limit at which pitch may not be effectively coded (around 1000 pps). Thus, as a further example, the electrodes belonging to a certain group could (in random or deterministic order) be stimulated at a rate derived from $F_x$ and the number of electrodes in the group so that the electrode-specific rate is below a certain pitch saturation limit and the aggregate group rate equals $F_x$.

Within each electrode group, channels are stimulated using the stimulation amplitude function A, which can, for example, define a constant stimulation amplitude across the group, or, as another example, define a stimulation profile. The stimulation profile could, e.g., also be derived from the non-linear properties of the basilar membrane and the adaptive function of the inner hair cells. The profile could also reflect other aspects of electrical stimulation of the cochlea, like, e.g., channel interactions. To keep interactions between adjacent groups low, smaller amplitudes could be used at the edges of a group than in the center of a group.

However, if a grouped stimulation channel transmits a temporal code (as, for example, in Fine Structure Processing (FSP)), then the temporal information can be corrupted by the channel selection process. That is, the stimulation channel with the temporal code may not be selected for stimulation if N other channels happen to have greater signal envelope amplitudes.

Low frequency stimulation electrodes are more salient in fasciculating phase locking of the auditory nerve higher frequency stimulation electrodes. Thus, in an N-of-M selection arrangement, only signal channels with the highest envelope amplitude are selected, which neglects the ability of the auditory nerve to process the phase information of the concerned channel. Thus, it may be advantageous for embodiments of the present invention to give preference lower-frequency signal channels when selecting the N signal channels. For example, the signal channels may gain priority based on a channel wise adjustable weighting arrangement (such as the signal envelope amplitude) wherein channel selection is based on the weighted channel feature. Thus, embodiments of the present invention also are directed to systems, methods and computer program products for activating stimulation electrodes in cochlear implant electrode based on channel-specific weighting factors favoring lower frequencies.

Referring to the system shown in FIG. 9, Preprocessor Filter Bank 901 processes an input acoustic audio signal to generate band pass signals $B_1$ to $B_M$ that each represent an associated band of audio frequencies. Information Extractor 902 extracts stimulation signal information from the band pass signals $B_1$ to $B_M$ based on assigning them to corresponding electrode stimulation groups that each contain one or more stimulation electrodes, and generates a set of stimulation event signals $S_1$ to $S_M$ for each electrode stimulation group that define electrode stimulation timings and amplitudes. For example, Information Extractor 902 may generate the stimulation event signals $S_1$ to $S_M$ based on a group pulse rate defined for each electrode stimulation group.

Pulse Selector 903 selects a set of N electrode stimulation signals $A_1$ to $A_N$ from the M stimulation event signals $S_1$ to $S_M$ based on a pulse weighting function that uses channel-specific weighting factors favoring lower frequencies for activating the stimulation electrodes to stimulate neighboring audio nerve tissue. In specific embodiments, the Pulse Selector 903 may select the set of electrode stimulation signals $A_1$ to $A_N$ in a recurring stimulation cycle based on the electrode stimulation groups as described above, for example, so as to sequentially activate a single stimulation electrode in each electrode stimulation group in each stimulation cycle, or to simultaneously activate at least two stimulation electrodes in at least one of the electrode stimulation groups in each stimulation cycle. Or, for at least one stimulation group, the Pulse Selector 903 may vary over time which specific stimulation electrodes are activated in each stimulation cycle. Pulse Selector 903 may generate the electrode stimulation signals for each electrode stimulation group based on one or more non-linear response characteristics of the stimulated nerve tissue. For example, the one or more non-linear response characteristics may reflect spatial interaction between the stimulation electrodes.

Pulse Selector 903 may select the electrode stimulation signals $A_1$ to $A_N$ so as to sequentially activate the stimulation electrodes within each electrode stimulation group. Or the pulse selector may select the electrode stimulation signals $A_1$ to $A_N$ so as to simultaneously activate the stimulation electrodes within at least one electrode stimulation group. Pulse Shaper 904 develops the electrode stimulation signals $A_1$ to $A_N$ from the Pulse Selector 903 into a set of output electrode pulses $E_1$ to $E_N$ to the stimulation electrodes based on patient specific factors.

FIG. 10 shows an example of such an embodiment starting from the stimulation arrangement shown in FIG. 5 and extending it with the weighting factors w(i). If the weighting factors w(i) are chosen appropriately so that their value is lower for lower frequency signal channels that are contained in one stimulation group, then this will lead to a preference for lower frequency channels as desired. For example, channel weighting factors as: w(1)=1 and w(2)=0.5 will give Channel 1 a preference by a factor of 2 over Channel 2.

FIG. 11 shows another example using channel specific weighting factors based on a more sophisticated weighting scheme. The first stimulation group contains the 6 signal channels with lowest frequencies (i.e., the 6 most apical stimulation electrodes in the cochlea). Out of this first stimulation group, 2 channels are selected each stimulation cycle for parallel stimulation as denoted by "2P". The remaining stimulation groups place higher frequency channels in stimulation groups of two paired channels, where each stimulation cycle, one channel in each group is stimulated. This grouping scheme results in a short stimulation frame, as the first stimulation group of 6 channels uses the same amount of time for stimulation as does just one single channel by itself Possible channel-specific weights might be: w(1)=1, w(2)=0.9, w(3) =0.8, w(4)=0.7, w(5)=0.6, w(6)=0.5 for the first stimulation group. This will give Channel 1 a preference by a factor 2 over Channel 6 and by a less in-between factor for Channels 2-5. For the higher frequency channels, weights w(7)=w(9)=w(11)=1 and w(8)=w(10)=w(12)=0.5 would ensure privilege of lower frequency channels.

Such low-frequency preferred channel weighting factors preserves important low-frequency information. This is important because the low frequency channels contain the fundamental frequency which is the most dominant cue for speech understanding. And if the fine time structure is transmitted via the coding strategy, then the fine structure of low frequencies also is preserved. The fine time structure of the lower frequency is more important than the fine time structure of higher frequencies because phase locking of the auditory nerve is much stronger for low frequencies and disappears for most of the CI users beyond 300 Hz.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable stimulation arrangement for generating electrode stimulation signals for stimulation electrodes in a cochlear implant, the arrangement comprising:
    a preprocessor filter bank for processing an input acoustic audio signal to generate a plurality of band pass signals each representing an associated band of audio frequencies;
    an information extractor for extracting stimulation signal information from the band pass signals based on assigning the band pass signals to a plurality of electrode stimulation groups each containing one or more stimulation electrodes, and generating a set of stimulation event signals for each electrode stimulation group that define electrode stimulation timings and amplitudes;
    a pulse selector for selecting a set of electrode stimulation signals from the stimulation event signals in a recurring stimulation cycle based on the electrode stimulation groups based on a pulse weighting function that uses channel-specific weighting factors favoring lower frequencies for activating the stimulation electrodes to stimulate neighboring audio nerve tissue, wherein for at least one stimulation group the pulse selector varies over time which specific stimulation electrodes are activated in each stimulation cycle; and
    a pulse shaper for developing the electrode stimulation signals into a set of output electrode pulses to the stimulation electrodes based on patient specific factors.

2. An arrangement according to claim 1, wherein the pulse selector selects the electrode stimulation signals so as to sequentially activate a single stimulation electrode in each electrode stimulation group in each stimulation cycle.

3. An arrangement according to claim 1, wherein the pulse selector selects the electrode stimulation signals so as to simultaneously activate at least two stimulation electrodes in at least one of the electrode stimulation groups in each stimulation cycle.

4. An arrangement according to claim 1, wherein the information extractor further generates the stimulation event signals based on a group pulse rate defined for each electrode stimulation group.

5. An arrangement according to claim 1, wherein the pulse selector further generates the electrode stimulation signals for each electrode stimulation group based on one or more non-linear response characteristics of the stimulated nerve tissue.

6. An arrangement according to claim 5, wherein the one or more non-linear response characteristics reflects spatial interaction between the stimulation electrodes.

7. An arrangement according to claim 1, wherein the pulse selector selects the electrode stimulation signals so as to sequentially activate the stimulation electrodes within each electrode stimulation group.

8. An arrangement according to claim 1, wherein the pulse selector selects the electrode stimulation signals so as to simultaneously activate the stimulation electrodes within at least one electrode stimulation group.

9. An arrangement according to claim 1, wherein the pulse weighting function uses channel specific weighting factors that are constant over time.

10. An arrangement according to claim 1, wherein the pulse weighting function uses channel specific weighting factors that vary over time.

11. A computer program product for use on a computer system for activating stimulation electrodes in a cochlear implant, the computer program product comprising a non-transitory computer usable medium having computer readable program code thereon, the computer readable program code including:
- program code for processing an input acoustic audio signal to generate a plurality of band pass signals each representing an associated band of audio frequencies;
- program code for extracting stimulation signal information from the band pass signals based on assigning the band pass signals to a plurality of electrode stimulation groups each containing one or more stimulation electrodes, and generating a set of stimulation event signals for each electrode stimulation group that define electrode stimulation timings and amplitudes;
- program code for selecting a set of electrode stimulation signals from the stimulation event signals in a recurring stimulation cycle based on the electrode stimulation groups based on a pulse weighting function that uses channel-specific weighting factors favoring lower frequencies for activating the stimulation electrodes to stimulate neighboring audio nerve tissue wherein for at least one stimulation group the program code for selecting a set of electrode stimulation signals varies over time which specific stimulation electrodes are activated in each stimulation cycle; and
- program code for developing the electrode stimulation signals into the set of output electrode pulses based on patient specific factors.

12. An arrangement according to claim 11, wherein the program code for selecting a set of electrode stimulation signals selects the electrode stimulation signals so as to sequentially activate a single stimulation electrode in each electrode stimulation group in each stimulation cycle.

13. An arrangement according to claim 11, wherein the program code for selecting a set of electrode stimulation signals selects the electrode stimulation signals so as to simultaneously activate at least two stimulation electrodes in at least one of the electrode stimulation groups in each stimulation cycle.

14. A product according to claim 11, wherein the program code for extracting stimulation signal information further generates the stimulation event signals based on a group pulse rate defined for each electrode stimulation group.

15. A product according to claim 11, wherein the program code for selecting a set of electrode stimulation signals further generates the electrode stimulation signals for each electrode stimulation group based on one or more non-linear response characteristics of the stimulated nerve tissue.

16. A product according to claim 15, wherein the one or more non-linear response characteristics reflects spatial interaction between the stimulation electrodes.

17. A product according to claim 11, wherein the program code for selecting a set of electrode stimulation signals selects the electrode stimulation signals so as to sequentially activate the stimulation electrodes within each electrode stimulation group.

18. A product according to claim 11, wherein the program code for selecting a set of electrode stimulation signals selects the electrode stimulation signals so as to simultaneously activate the stimulation electrodes within at least one electrode stimulation group.

19. A product according to claim 11, wherein the pulse weighting function uses channel specific weighting factors that are constant over time.

20. A product according to claim 11, wherein the pulse weighting function uses channel specific weighting factors that vary over time.

21. A method of activating stimulation electrodes in a cochlear implant electrode, the method comprising:
- processing an input acoustic audio signal to generate a plurality of band pass signals each representing an associated band of audio frequencies;
- extracting stimulation signal information from the band pass signals based on assigning the band pass signals to a plurality of electrode stimulation groups each containing one or more stimulation electrodes, and generating a set of stimulation event signals for each electrode stimulation group that define electrode stimulation timings and amplitudes;
- selecting a set of electrode stimulation signals from the stimulation event signals in a recurring stimulation cycle based on the electrode stimulation groups based on a pulse weighting function that uses channel-specific weighting factors favoring lower frequencies for activating the stimulation electrodes to stimulate neighboring audio nerve tissue, wherein for at least one stimulation group, selecting a set of electrode stimulation signals includes varying over time which specific stimulation electrodes are activated in each stimulation cycle; and
- developing the electrode stimulation signals into the set of output electrode pulses based on patient specific factors.

22. A method according to claim 21, wherein selecting a set of electrode stimulation signals includes selecting the electrode stimulation signals so as to sequentially activate a single stimulation electrode in each electrode stimulation group in each stimulation cycle.

23. A method according to claim 21, wherein selecting a set of electrode stimulation signals includes selecting the electrode stimulation signals so as to simultaneously activate at least two stimulation electrodes in at least one of the electrode stimulation groups in each stimulation cycle.

24. A method according to claim 21, wherein extracting stimulation signal information includes generating the stimulation event signals based on a group pulse rate defined for each electrode stimulation group.

25. A method according to claim 21, wherein selecting a set of electrode stimulation signals includes generating the electrode stimulation signals for each electrode stimulation group based on one or more non-linear response characteristics of the stimulated nerve tissue.

26. A method according to claim 25, wherein the one or more non-linear response characteristics reflects spatial interaction between the stimulation electrodes.

27. A method according to claim 21, wherein selecting a set of electrode stimulation signals includes selecting the electrode stimulation signals so as to sequentially activate the stimulation electrodes within each electrode stimulation group.

28. A method according to claim 21, wherein selecting a set of electrode stimulation signals includes selecting the electrode stimulation signals so as to simultaneously activate the stimulation electrodes within at least one electrode stimulation group.

29. A method according to claim 21, wherein the pulse weighting function uses channel specific weighting factors that are constant over time.

30. method according to claim 21, wherein the pulse weighting function uses channel specific weighting factors that vary over time.

31. An implantable stimulation arrangement for generating electrode stimulation signals for stimulation electrodes in a cochlear implant, the arrangement comprising:

a preprocessor filter bank for processing an input acoustic audio signal to generate a plurality of band pass signals each representing an associated band of audio frequencies;

an information extractor for extracting stimulation signal information from the band pass signals based on assigning the band pass signals to a plurality of electrode stimulation groups each containing one or more stimulation electrodes, and generating a set of stimulation event signals for each electrode stimulation group based on a group pulse rate defined for each electrode stimulation group to define electrode stimulation timings and amplitudes;

a pulse selector for selecting a set of electrode stimulation signals from the stimulation event signals based on a pulse weighting function that uses channel-specific weighting factors favoring lower frequencies for activating the stimulation electrodes to stimulate neighboring audio nerve tissue; and a pulse shaper for developing the electrode stimulation signals into a set of output electrode pulses to the stimulation electrodes based on patient specific factors.

32. An arrangement according to claim 31, wherein the pulse selector selects the set of electrode stimulation signals in a recurring stimulation cycle based on the electrode stimulation groups.

33. An arrangement according to claim 32, wherein for at least one electrode stimulation group the pulse selector varies over time which specific stimulation electrodes are activated in each stimulation cycle.

34. An arrangement according to claim 31, wherein the pulse weighting function uses channel specific weighting factors that are constant over time.

35. An arrangement according to claim 31, wherein the pulse weighting function uses channel specific weighting factors that vary over time.

36. A computer program product for use on a computer system for activating stimulation electrodes in a cochlear implant, the computer program product comprising a non-transitory computer usable medium having computer readable program code thereon, the computer readable program code including:

program code for processing an input acoustic audio signal to generate a plurality of band pass signals each representing an associated band of audio frequencies;

program code for extracting stimulation signal information from the band pass signals based on assigning the band pass signals to a plurality of electrode stimulation groups each containing one or more stimulation electrodes, and generating a set of stimulation event signals for each electrode stimulation group based on a group pulse rate defined for each electrode stimulation group to define electrode stimulation timings and amplitudes;

program code for selecting a set of electrode stimulation signals from the stimulation event signals based on a pulse weighting function that uses channel-specific weighting factors favoring lower frequencies for activating the stimulation electrodes to stimulate neighboring audio nerve tissue; and program code for developing the electrode stimulation signals into the set of output electrode pulses based on patient specific factors.

37. A product according to claim 36, wherein the program code for selecting a set of electrode stimulation signals further selects the set of electrode stimulation signals in a recurring stimulation cycle based on the electrode stimulation groups.

38. A product according to claim 37, wherein for at least one electrode stimulation group the program code for selecting a set of electrode stimulation signals varies over time which specific stimulation electrodes are activated in each stimulation cycle.

39. A product according to claim 36, wherein the pulse weighting function uses channel specific weighting factors that are constant over time.

40. A product according to claim 36, wherein the pulse weighting function uses channel specific weighting factors that vary over time.

41. A method of activating stimulation electrodes in a cochlear implant electrode, the method comprising:

processing an input acoustic audio signal to generate a plurality of band pass signals each representing an associated band of audio frequencies;

extracting stimulation signal information from the band pass signals based on assigning the band pass signals to a plurality of electrode stimulation groups each containing one or more stimulation electrodes, and generating a set of stimulation event signals for each electrode stimulation group based on a group pulse rate defined for each electrode stimulation group to define electrode stimulation timings and amplitudes;

selecting a set of electrode stimulation signals from the stimulation event signals based on a pulse weighting function that uses channel-specific weighting factors favoring lower frequencies for activating the stimulation electrodes to stimulate neighboring audio nerve tissue; and developing the electrode stimulation signals into the set of output electrode pulses based on patient specific factors.

42. A method according to claim 41, wherein selecting a set of electrode stimulation signals includes selecting the set of electrode stimulation signals in a recurring stimulation cycle based on the electrode stimulation groups.

43. A method according to claim 42, wherein for at least one electrode stimulation group, selecting a set of electrode stimulation signals includes varying over time which specific stimulation electrodes are activated in each stimulation cycle.

44. A method according to claim 41, wherein the pulse weighting function uses channel specific weighting factors that are constant over time.

45. A method according to claim 41, wherein the pulse weighting function uses channel specific weighting factors that vary over time.

46. An implantable stimulation arrangement for generating electrode stimulation signals for stimulation electrodes in a cochlear implant, the arrangement comprising:

a preprocessor filter bank for processing an input acoustic audio signal to generate a plurality of band pass signals each representing an associated band of audio frequencies;

an information extractor for extracting stimulation signal information from the band pass signals based on assigning the band pass signals to a plurality of electrode stimulation groups each containing one or more stimulation electrodes, and generating a set of stimulation event signals for each electrode stimulation group that define electrode stimulation timings and amplitudes;

a pulse selector for selecting a set of electrode stimulation signals from the stimulation event signals based on a pulse weighting function that uses time-constant channel-specific weighting factors favoring lower frequencies for activating the stimulation electrodes to stimulate neighboring audio nerve tissue; and a pulse shaper for developing the electrode stimulation signals into a set of output electrode pulses to the stimulation electrodes based on patient specific factors.

47. An arrangement according to claim 46, wherein the pulse selector selects the set of electrode stimulation signals in a recurring stimulation cycle based on the electrode stimulation groups.

48. An arrangement according to claim 47, wherein for at least one electrode stimulation group the pulse selector varies over time which specific stimulation electrodes are activated in each stimulation cycle.

49. An arrangement according to claim 46, wherein the information extractor further generates the stimulation event signals based on a group pulse rate defined for each electrode stimulation group.

50. A computer program product for use on a computer system for activating stimulation electrodes in a cochlear implant, the computer program product comprising a non-transitory computer usable medium having computer readable program code thereon, the computer readable program code including:
program code for processing an input acoustic audio signal to generate a plurality of band pass signals each representing an associated band of audio frequencies;
program code for extracting stimulation signal information from the band pass signals based on assigning the band pass signals to a plurality of electrode stimulation groups each containing one or more stimulation electrodes, and generating a set of stimulation event signals for each electrode stimulation group that define electrode stimulation timings and amplitudes;
program code for selecting a set of electrode stimulation signals from the stimulation event signals based on a pulse weighting function that uses time-constant channel-specific weighting factors favoring lower frequencies for activating the stimulation electrodes to stimulate neighboring audio nerve tissue; and
program code for developing the electrode stimulation signals into the set of output electrode pulses based on patient specific factors.

51. A product according to claim 50, wherein the program code for selecting a set of electrode stimulation signals further selects the set of electrode stimulation signals in a recurring stimulation cycle based on the electrode stimulation groups.

52. A product according to claim 51, wherein for at least one electrode stimulation group the program code for selecting a set of electrode stimulation signals varies over time which specific stimulation electrodes are activated in each stimulation cycle.

53. A product according to claim 50, wherein the program code for extracting stimulation signal information further generates the stimulation event signals based on a group pulse rate defined for each electrode stimulation group.

54. A method of activating stimulation electrodes in a cochlear implant electrode, the method comprising:
processing an input acoustic audio signal to generate a plurality of band pass signals each representing an associated band of audio frequencies;
extracting stimulation signal information from the band pass signals based on assigning the band pass signals to a plurality of electrode stimulation groups each containing one or more stimulation electrodes, and generating a set of stimulation event signals for each electrode stimulation group that defines electrode stimulation timings and amplitudes;
selecting a set of electrode stimulation signals from the stimulation event signals based on a pulse weighting function that uses time-constant channel-specific weighting factors favoring lower frequencies for activating the stimulation electrodes to stimulate neighboring audio nerve tissue; and
developing the electrode stimulation signals into the set of output electrode pulses based on patient specific factors.

55. A method according to claim 54, wherein selecting a set of electrode stimulation signals includes selecting the set of electrode stimulation signals in a recurring stimulation cycle based on the electrode stimulation groups.

56. A method according to claim 55, wherein selecting a set of electrode stimulation signals selecting the set of electrode stimulation signals in a recurring stimulation cycle based on the electrode stimulation groups.

57. A method according to claim 54, wherein for at least one electrode stimulation group, selecting a set of electrode stimulation signals includes varying over time which specific stimulation electrodes are activated in each stimulation cycle.

58. An implantable stimulation arrangement for generating electrode stimulation signals for stimulation electrodes in a cochlear implant, the arrangement comprising:
a preprocessor filter bank for processing an input acoustic audio signal to generate a plurality of band pass signals each representing an associated band of audio frequencies;
an information extractor for extracting stimulation signal information from the band pass signals based on assigning the band pass signals to a plurality of electrode stimulation groups each containing one or more stimulation electrodes, and generating a set of stimulation event signals for each electrode stimulation group that define electrode stimulation timings and amplitudes;
a pulse selector for selecting a set of electrode stimulation signals from the stimulation event signals based on a pulse weighting function that uses time-varying channel-specific weighting factors favoring lower frequencies for activating the stimulation electrodes to stimulate neighboring audio nerve tissue; and
a pulse shaper for developing the electrode stimulation signals into a set of output electrode pulses to the stimulation electrodes based on patient specific factors.

59. An arrangement according to claim 58, wherein the pulse selector selects the set of electrode stimulation signals in a recurring stimulation cycle based on the electrode stimulation groups.

60. An arrangement according to claim 59, wherein for at least one electrode stimulation group the pulse selector varies over time which specific stimulation electrodes are activated in each stimulation cycle.

61. An arrangement according to claim 58, wherein the information extractor further generates the stimulation event signals based on a group pulse rate defined for each electrode stimulation group.

62. A computer program product for use on a computer system for activating stimulation electrodes in a cochlear implant, the computer program product comprising a non-transitory computer usable medium having computer readable program code thereon, the computer readable program code including:
program code for processing an input acoustic audio signal to generate a plurality of band pass signals each representing an associated band of audio frequencies;
program code for extracting stimulation signal information from the band pass signals based on assigning the band pass signals to a plurality of electrode stimulation groups each containing one or more stimulation electrodes, and generating a set of stimulation event signals for each electrode stimulation group that define electrode stimulation timings and amplitudes;

program code for selecting a set of electrode stimulation signals from the stimulation event signals based on a pulse weighting function that uses time-varying channel-specific weighting factors favoring lower frequencies for activating the stimulation electrodes to stimulate neighboring audio nerve tissue; and program code for developing the electrode stimulation signals into the set of output electrode pulses based on patient specific factors.

63. A product according to claim 62, wherein the program code for selecting a set of electrode stimulation signals further selects the set of electrode stimulation signals in a recurring stimulation cycle based on the electrode stimulation groups.

64. A product according to claim 63, wherein for at least one electrode stimulation group the program code for selecting a set of electrode stimulation signals varies over time which specific stimulation electrodes are activated in each stimulation cycle.

65. A product according to claim 62, wherein the program code for extracting stimulation signal information further generates the stimulation event signals based on a group pulse rate defined for each electrode stimulation group.

66. A method of activating stimulation electrodes in a cochlear implant electrode, the method comprising:

processing an input acoustic audio signal to generate a plurality of band pass signals each representing an associated band of audio frequencies;

extracting stimulation signal information from the band pass signals based on assigning the band pass signals to a plurality of electrode stimulation groups each containing one or more stimulation electrodes, and generating a set of stimulation event signals for each electrode stimulation group that defines electrode stimulation timings and amplitudes;

selecting a set of electrode stimulation signals from the stimulation event signals based on a pulse weighting function that uses time-varying channel-specific weighting factors favoring lower frequencies for activating the stimulation electrodes to stimulate neighboring audio nerve tissue; and developing the electrode stimulation signals into the set of output electrode pulses based on patient specific factors.

67. A method according to claim 66, wherein selecting a set of electrode stimulation signals includes selecting the set of electrode stimulation signals in a recurring stimulation cycle based on the electrode stimulation groups.

68. A method according to claim 67, wherein selecting a set of electrode stimulation signals selecting the set of electrode stimulation signals in a recurring stimulation cycle based on the electrode stimulation groups.

69. A method according to claim 66, wherein for at least one electrode stimulation group, selecting a set of electrode stimulation signals includes varying over time which specific stimulation electrodes are activated in each stimulation cycle.

* * * * *